United States Patent [19]

Honda et al.

[11] Patent Number: 5,152,277
[45] Date of Patent: Oct. 6, 1992

[54] CATHETER TUBE

[75] Inventors: Hiroaki Honda, Naha; Masahiro Nudeshima, Fuji, both of Japan

[73] Assignee: Terumo Kabushiki Kaisha, Tokyo, Japan

[21] Appl. No.: 460,063

[22] PCT Filed: Jul. 21, 1988

[86] PCT No.: PCT/JP88/00732
§ 371 Date: Feb. 26, 1990
§ 102(e) Date: Feb. 26, 1990

[87] PCT Pub. No.: WO89/00829
PCT Pub. Date: Feb. 9, 1989

[30] Foreign Application Priority Data

Jul. 23, 1987 [JP] Japan .................. 62-184557
Sep. 10, 1987 [JP] Japan .................. 62-227072
Sep. 25, 1987 [JP] Japan .................. 62-241478

[51] Int. Cl.⁵ ........................................ A61B 1/00
[52] U.S. Cl. .............................. 128/4; 128/6; 604/96; 604/101; 604/171; 606/15
[58] Field of Search ............... 128/4, 6, 398; 606/7, 606/14-17; 604/96, 159, 163, 171, 172, 101

[56] References Cited

U.S. PATENT DOCUMENTS

| | | | |
|---|---|---|---|
| 3,757,771 | 9/1973 | Ruegg et al. ............ | 604/163 |
| 3,825,001 | 7/1974 | Bennet et al. ............ | 604/163 |
| 4,057,065 | 11/1977 | Thow . | |
| 4,335,713 | 6/1982 | Komiya .................... | 128/6 |
| 4,444,462 | 4/1984 | Ono et al. ................ | 128/6 |
| 4,445,892 | 5/1984 | Hussein et al. . | |
| 4,573,966 | 3/1986 | Weikl et al. . | |
| 4,586,491 | 5/1986 | Carpenter ................ | 128/6 |
| 4,610,662 | 9/1986 | Weikl et al. . | |
| 4,669,465 | 6/1987 | Moore et al. ............ | 606/15 |
| 4,770,653 | 9/1988 | Shturman ................ | 604/96 |
| 4,832,023 | 5/1989 | Murphy-Chutorian et al. ..... | 604/96 |
| 4,846,171 | 7/1989 | Kauphusman et al. ........... | 606/15 |
| 4,863,440 | 9/1989 | Chin . | |

FOREIGN PATENT DOCUMENTS

| | | |
|---|---|---|
| 0227583 | 12/1986 | European Pat. Off. . |
| 2637133 | 2/1978 | Fed. Rep. of Germany ......... 128/6 |
| 2848484 | 5/1979 | Fed. Rep. of Germany . |
| 3326648 | 7/1983 | Fed. Rep. of Germany . |
| 53-685 | 1/1978 | Japan . |
| 56-41683 | 9/1981 | Japan . |
| 57-22887 | 5/1982 | Japan . |
| WO-A-83/01894 | 11/1982 | World Int. Prop. O. . |

*Primary Examiner*—Stephen C. Pellegrino
*Assistant Examiner*—Ralph A. Lewis
*Attorney, Agent, or Firm*—Frishauf, Holtz, Goodman & Woodward

[57] ABSTRACT

This invention relates to a catheter tube which is used for visualizing or medically treating the interior of a body cavity having a relatively small diameter, typically a blood vessel by inserting and leaving it in the body cavity.

The catheter tube of the invention includes at least one inflatable/contractible balloon disposed adjacent the distal end thereof, and its tube body is formed with a lumen for inflating the balloon, a lumen for injecting a liquid into the body cavity, and a lumen for accommodating a visualizing or therapeutic instrument. The invention is characterized in that the visualizing or therapeutic instrument is moved in a longitudinal direction of the tube to move its distal end into and out of the opening of the instrument accommodating lumen, ensuring a clear observation over a wide field, that the respective lumens can be commonly replaced by a multi-purpose lumen, allowing the tube to be reduced in diameter, that visualization between two balloons provides a clearer visual image, and that a bypass lumen is additionally provided to maintain a blood flow through the blood vessel even during observation, enabling long-term observation.

18 Claims, 9 Drawing Sheets

CATHETER TUBE

FIELD OF THE INVENTION

This invention relates to a catheter for insertion into a body cavity for visualizing the interior of the body cavity or medically treating the inner wall of the body cavity from outside the body, and more particularly, to a catheter tube for an endoscope or fiberscope.

BACKGROUND OF THE INVENTION

Endoscopes are inserted into a body cavity from outside the body to visualize the interior of the body cavity while allowing medical treatment including injection of a fluid medicine in the cavity wall and exposure to laser beams. They recently have attracted greater interest which has encouraged development efforts.

Endoscopes, especially those endoscopes for visualizing the interior of a thin body cavity, typically a blood vessel are of a configuration wherein a bundle of optical fibers for transmitting and receiving light is accommodated in a flexible catheter tube. The catheter tube is inserted into a blood vessel until it reaches a destined site where the light-transmitting fiber (or light guide) projects light from its distal end to an area under observation and the light-receiving fiber (or image fiber) receives the reflected light at the distal end and conducts it to an imaging section where a visual image is provided for observation.

For visual observation of the interior of a blood vessel by means of an endoscope, the blood which obstructs a view to a site under observation must be removed before observation can be done.

However, prior art catheter tubes used in endoscopes have several problems as described below.

First Problem

In a prior art endoscope, an optical fiber bundle with a light guide and an image fiber joined together has a distal portion secured substantially flush with the distal end of the catheter tube. When the catheter tube is inserted into the body cavity, the distal end of the optical fiber bundle makes contact with an instrument (or guide catheter) for assisting in inserting the catheter tube so that the distal or light-receiving face of the image fiber is flawed. The resulting visual image becomes vague.

The optical fiber bundle is secured to the catheter tube by aligning the bundle in the catheter tube with their distal ends flush and bonding a distal portion of the bundle with an adhesive. Thus the distal face of the optical fiber bundle tends to be contaminated with the adhesive during the manufacture process. This also adversely affects the clarity of a visual image.

To prevent damage to the distal face of optical fibers, it might be possible to secure the optical fiber bundle in the lumen of the catheter tube with the distal end of the bundle retracted. However the inner wall of the lumen can be an obstacle to a clear view, this design imposes visualization difficulties or allows visualization over only a limited field of view.

Further, prior art endoscopes have a drawback that cumbersome steps must be taken when it is desired to change the site under observation in the body cavity (in a longitudinal direction of the body cavity). It is necessary to first contract the balloon to disengage the catheter tube from the body cavity, then move the catheter tube in a longitudinal direction of the body cavity to the next destined site, inflate the balloon again to retain the catheter tube relative to the body cavity, and inject a clear fluid before the new site can be visualized.

Second Problem

In the prior art, the blood which obstructs a view was removed by inflating the balloon around the periphery of the tube to shut off blood flow, and then injecting a clear fluid such as physiological saline to a site to be observed to sweep away the blood therefrom and fill the space with the clear fluid instead.

Therefore, in the prior art catheter tube constituting an endoscope, a tube body was formed with a special lumen for accommodating an optical fiber, a first special lumen was needed to provide as a flowpath for a fluid for inflating or contracting the balloon, and a second special lumen was needed to act as a flowpath for injecting a clear fluid for displacing the blood.

Since the tube body was formed with three individual lumens specialized for different purposes and the individual lumens were required to have sufficient predetermined inner diameters to perform their own function, it was very difficult to reduce the diameter of the catheter tube.

A catheter tube which is devoid of a balloon and hence, does not have a special lumen for balloon inflation may be contemplated. Since blockage of blood flow by the balloon does not occur, it is difficult to insure a clear view only by injection of clear fluid. Hence, such a catheter will not provide consistently clear images. An undesirably large amount of clear fluid must be injected to obtain a clearer view, resulting in a loss of safety to the human body.

Third Problem

The above-mentioned method for the displacement or blood by inflating the balloon to shut off blood flow would sometimes invite a reverse flow of blood in the case of an arterial examination, for example. Further only a limited time is allowed for observation because it is not recommended in consideration of safety to the human body to protract the shutting off of a blood flow.

DISCLOSURE OF THE INVENTION

An object of the present invention is to provide a catheter tube:

which ensures clear visualization over a wide range of view when constructed as endoscope, for example, which is of a simple structure to insure observation and medical treatment of a body cavity, which can be reduced in diameter without a loss of performance as compared with the prior art catheter tubes, and which allows for observation and medical treatment of a body cavity, especially a blood vessel over a prolonged period of time.

Through extensive investigations, the inventors have found that the following constructions are effective in achieving this and other objects.

A first form of the invention is a construction wherein a bundle of optical fibers serving as a visualizing or therapeutic instrument is movable through a catheter tube in an axial direction thereof such that the distal end of the optical fiber bundle is retractable in an optical fiber accommodating lumen when the catheter tube is inserted into a body cavity, and the distal end of the optical fiber bundle is projectable beyond the catheter tube for observation when the interior of the body cavity is visualized or medically treated.

A second form of the invention is a construction wherein a lumen for accommodating an optical fiber, a lumen for inflating a balloon, and a lumen for injecting a clear liquid are commonly provided by a single lumen formed in a tube body.

A third form of the invention is a catheter tube having a construction wherein a tube body is provided with first and second balloons adapted to be inflated to shut off a blood flow and the space between the balloons is filled with a clear liquid replacing the visibility impeding blood, enabling observation, and wherein a bypass for communication between the outsides of the balloons permits blood to flow therethrough during observation.

More specifically, the first form of the invention provides a catheter tube for use by inserting into a body cavity, comprising a tube body, at least one inflatable/contractible balloon attached around the outer peripheral wall of a distal portion of said tube body, lumens defined in said tube body and open to the distal portion of said tube body for accommodating an instrument and injecting a fluid, respectively, a lumen defined in said tube body in flow communication with the interior of said balloon for inflating said balloon, a visualizing or therapeutic instrument accommodated in said instrument accommodating lumen for visualizing or medically treating the interior of the body cavity, and manipulator means provided at a proximal side of said catheter tube for moving said visualizing or therapeutic instrument through the tube body in an axial direction thereof and locating said visualizing or therapeutic instrument at a required position relative to said tube body while maintaining said instrument accommodating lumen fluid tight at the proximal side.

Several preferred embodiments of the first form are described below.

(i) The visualizing or therapeutic instrument is a bundle of optical fibers and the inner diameter of said instrument accommodating lumen is 1.1 to 3.0 times the outer diameter of the optical fiber bundle.

(ii) The surface of said optical fiber bundle and/or the inner surface of said instrument accommodating lumen has been subjected to lubricating treatment.

(iii) The manipulator means includes a cylinder-shaped female connector connected for communication with said instrument accommodating lumen at the proximal end, and a piston-shaped male connector received in the bore of said female connector through a sealing member and having said visualizing or therapeutic instrument secured thereto.

(iv) The manipulator means includes a closed bellows connected for communication with said instrument accommodating lumen at the proximal end and having said visualizing or therapeutic instrument secured at a proximal end thereof, and a holder receiving said bellows for limiting the extent of expansion of said bellows.

(v) The visualizing or therapeutic instrument is moved by said manipulator means over the range from the protective position at which the distal end of said visualizing or therapeutic instrument is within said instrument accommodating lumen to the position at which the distal end of said visualizing or therapeutic instrument projects 0 to 20 mm beyond the distal opening of said instrument accommodating lumen.

The second form of the invention provides a catheter tube for use by insertion into a body cavity, comprising a tube body, at least one inflatable/contractible balloon attached around the outer peripheral wall of a distal portion of said tube body, a multi-purpose lumen defined in said tube body, open to the distal portion of said tube body and adapted to accommodate a visualizing or therapeutic instrument for visualizing or medically treating the interior of the body cavity, said lumen allowing a fluid to flow between said visualizing or therapeutic instrument and the inner wall of said lumen, and a side aperture communicating the interior of said multi-purpose lumen with the interior of said balloon.

One preferred embodiment of the second form is described below.

(vi) The visualizing or therapeutic instrument is a bundle of optical fibers and the inner diameter of said multi-purpose lumen is 1.1 to 5.0 times the outer diameter of the optical fiber bundle.

The third form of the invention provides a catheter tube for use by insertion into a body cavity, comprising a tube body, a first inflatable/contractible balloon attached around the outer peripheral wall of a distal portion of said tube body, a second inflatable/contractible balloon attached around the outer peripheral wall of said tube body at a predetermined spacing from the first balloon toward a proximal side, lumens in flow communication with the interior of said first and second balloons for inflating said balloons, a lumen for accommodating a visualizing or therapeutic instrument for visualizing or medically treating the interior of the body cavity between said first and second balloons, a lumen open at the outer peripheral wall of said tube body between said first and second balloons for injecting a fluid, and a bypass lumen communicating with a first opening in the tube body on a distal side with respect to said first balloon and a second opening in the tube body on a proximal side with respect to said second balloon, said first balloon at the proximal side being spaced 1 to 100 mm from said second balloon at the distal side.

Further in the first, second, and third forms, preferably the balloon when inflated has a minimum diameter at least substantially equal to the maximum inner diameter of the body cavity into which the catheter tube is to be inserted.

BRIEF DESCRIPTION OF THE INVENTION

Figure 1:
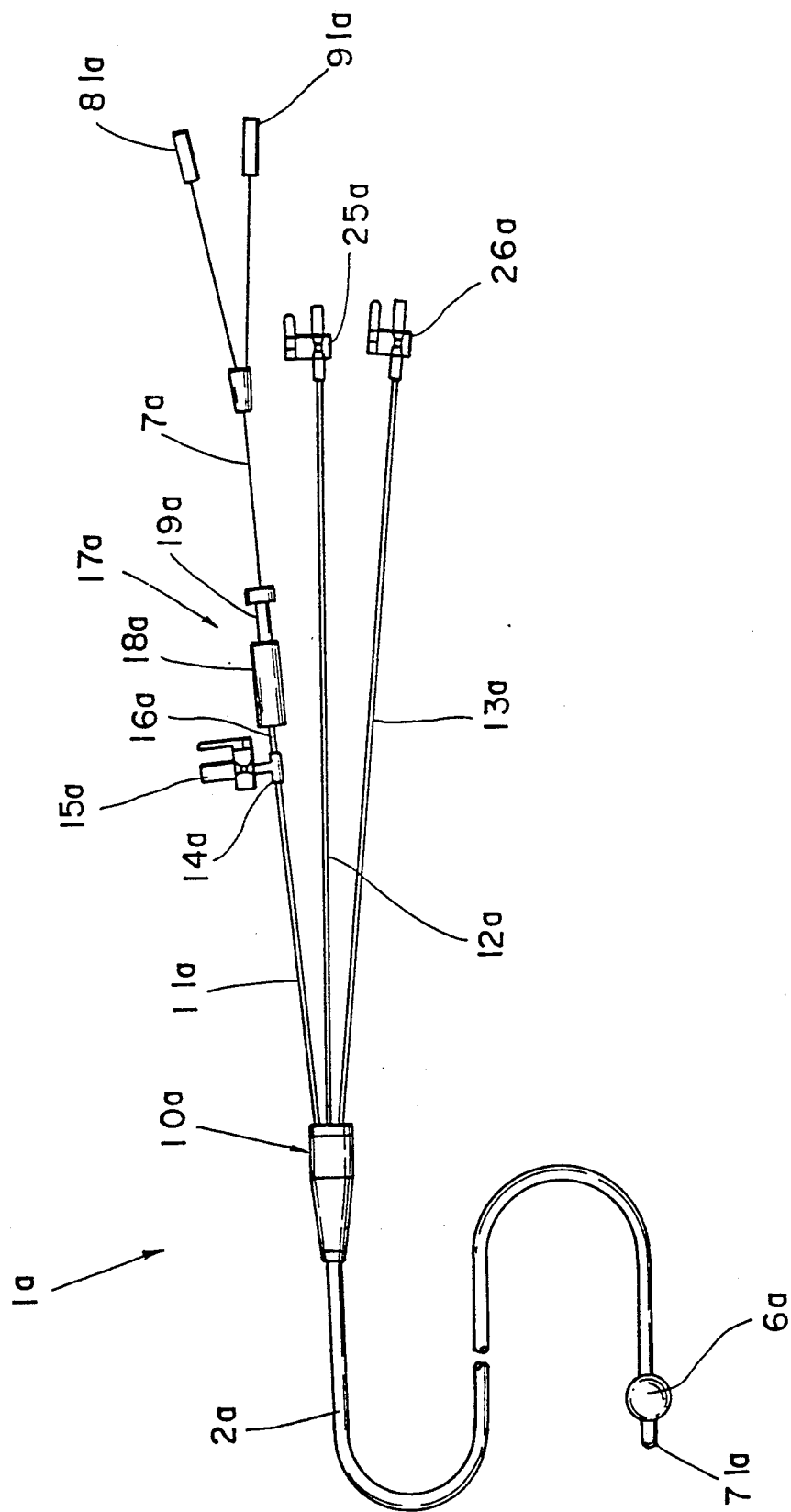
FIG. 1 is a side view of a catheter tube according to one embodiment of the present invention.
Figure 2:
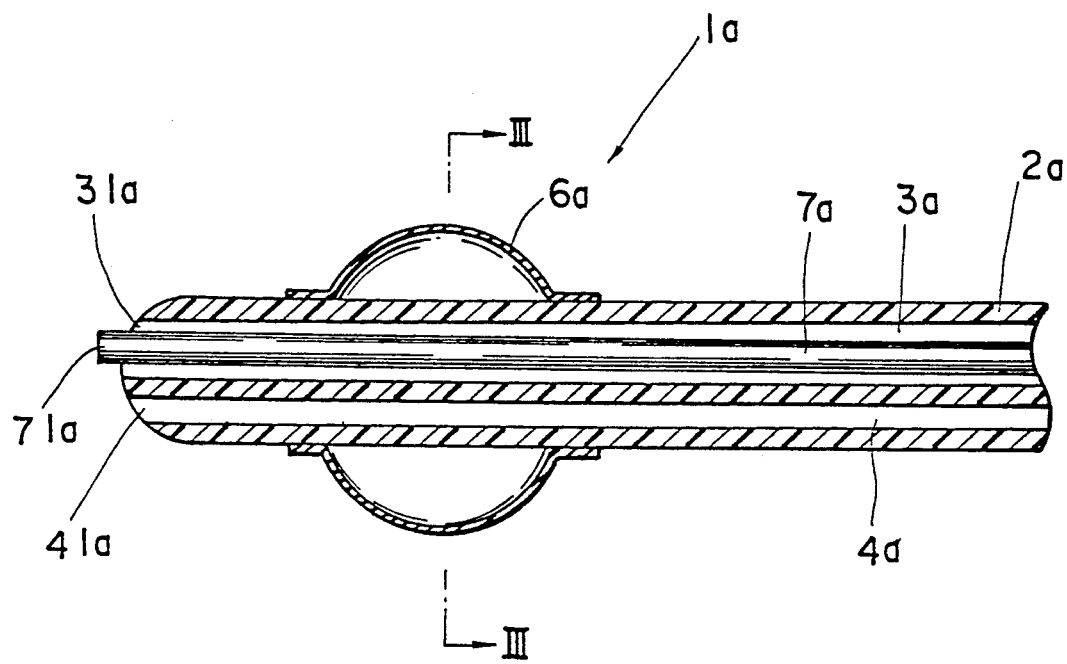
FIG. 2 is a fragmental axial cross-sectional view showing the construction of a distal end portion of the catheter tube shown in FIG. 1.
Figure 6:
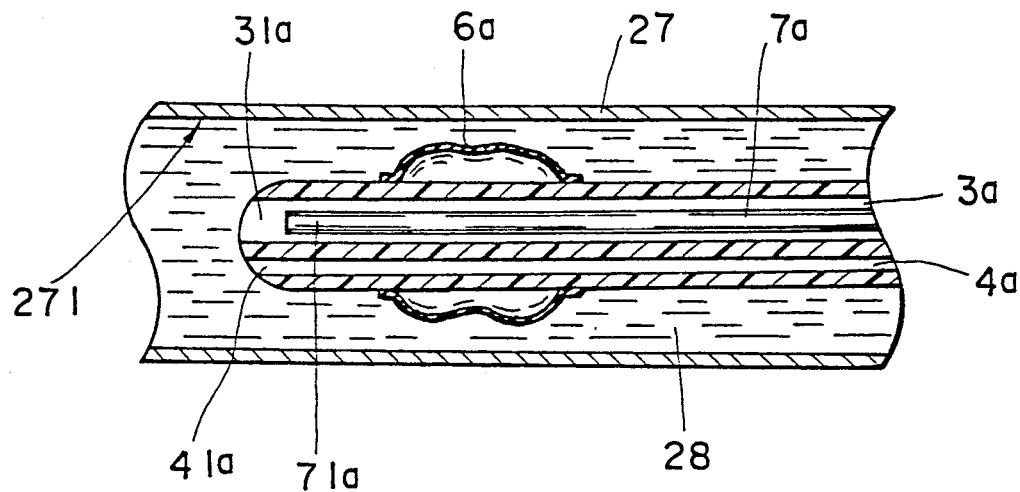
Figure 7:
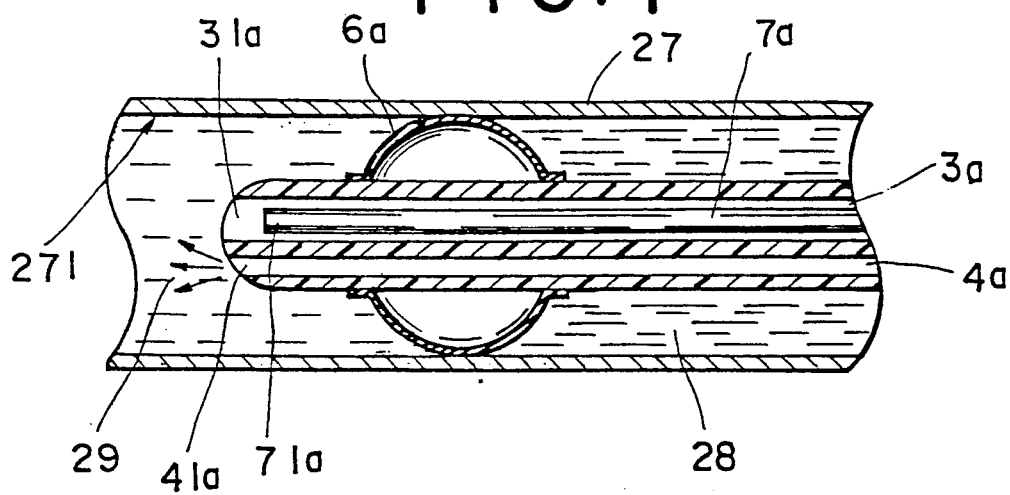
Figure 8:
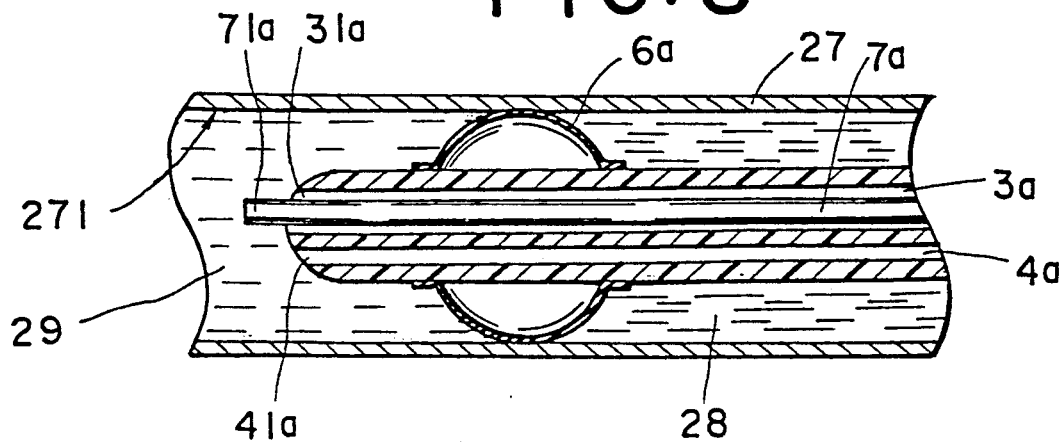

FIGS. 6, 7, and 8 are fragmental cross-sectional views showing the catheter tube of FIGS. 1 and 2 during its use.

Figure 9:
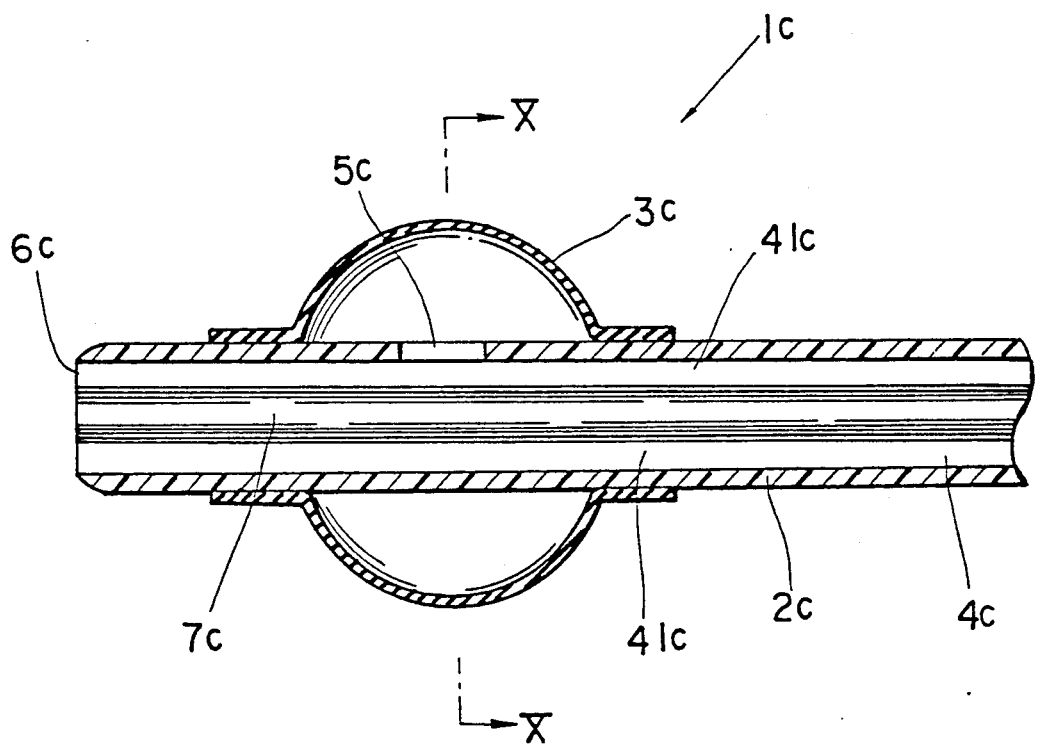

FIG. 9 is a fragmental axial cross-sectional view of a catheter tube according to another embodiment of the present invention.

Figure 10:
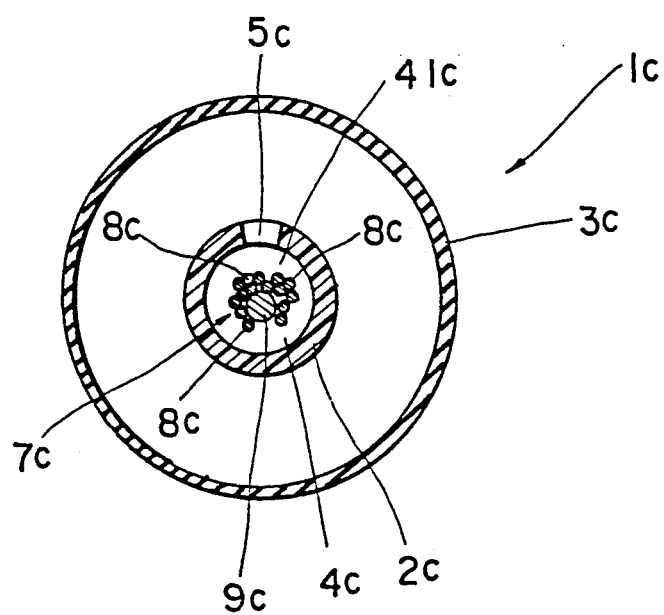

FIG. 10 is a cross-sectional view taken along lines X—X in FIG. 9.

Figure 11:
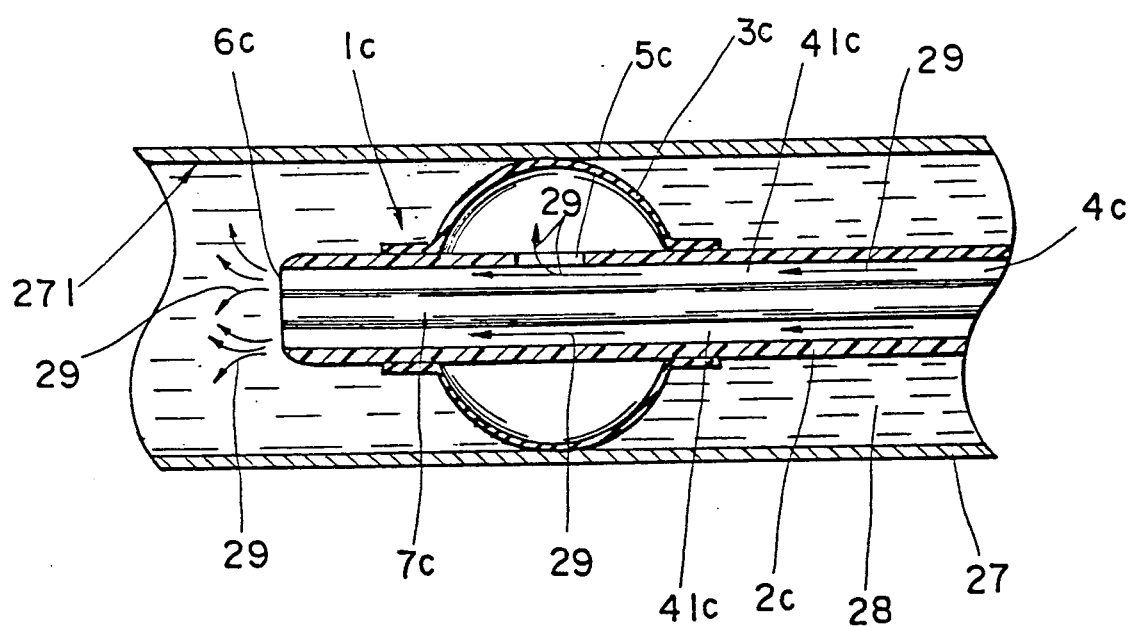

FIG. 11 is a fragmental cross-sectional view showing the catheter tube of the invention during its use.

Figure 12:
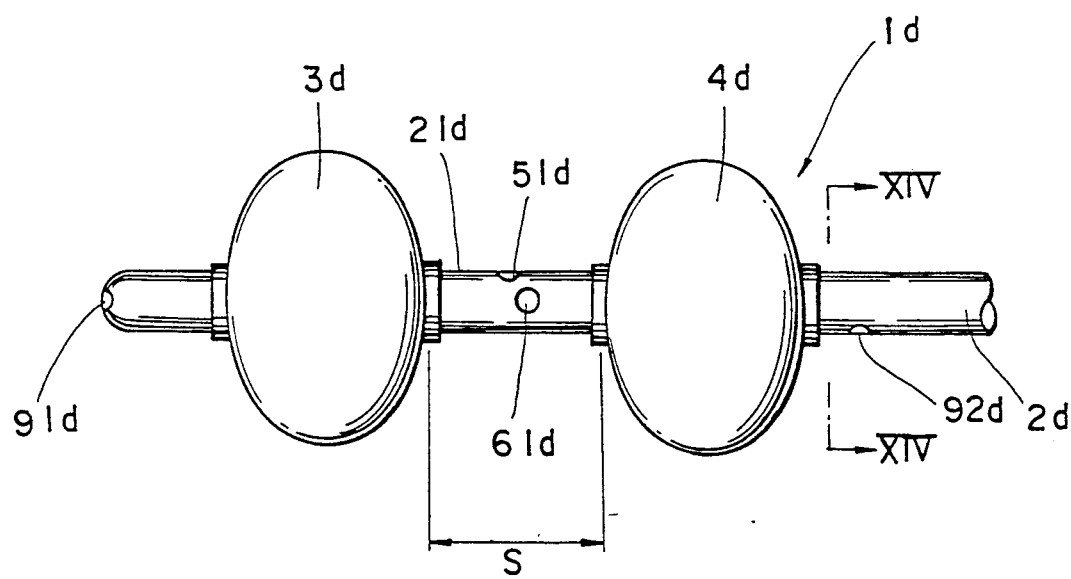

FIG. 12 is a side view of a catheter tube according to a further embodiment of the present invention.

Figure 13:
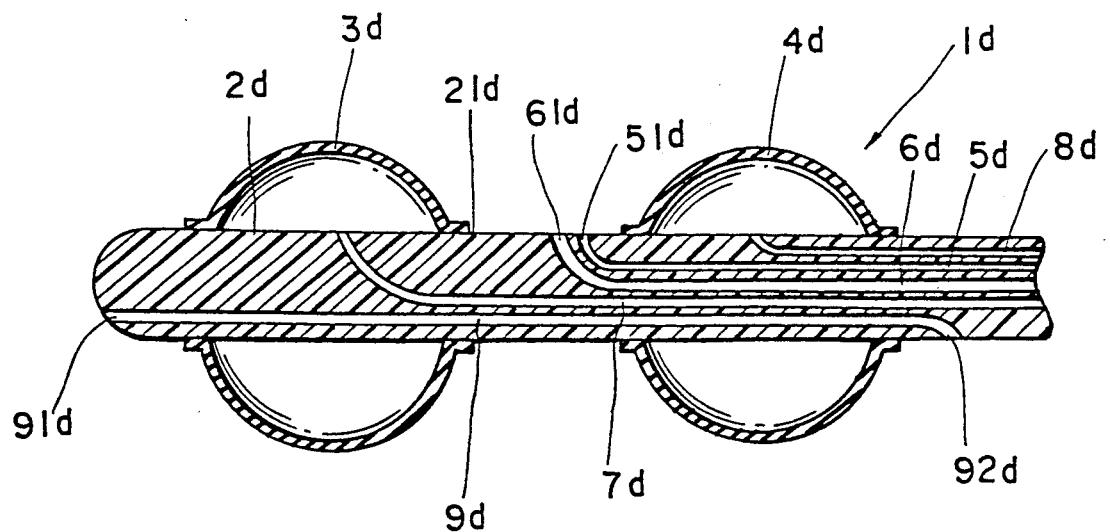

FIG. 13 is an axial cross-sectional view of the catheter tube of FIG. 12.

Figure 14:
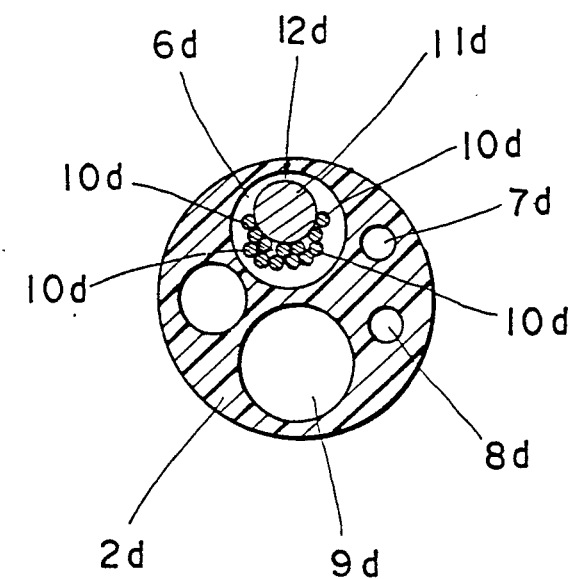

FIG. 14 is a cross-sectional view taken along lines XIV—XIV in FIG. 12.

Figure 15:
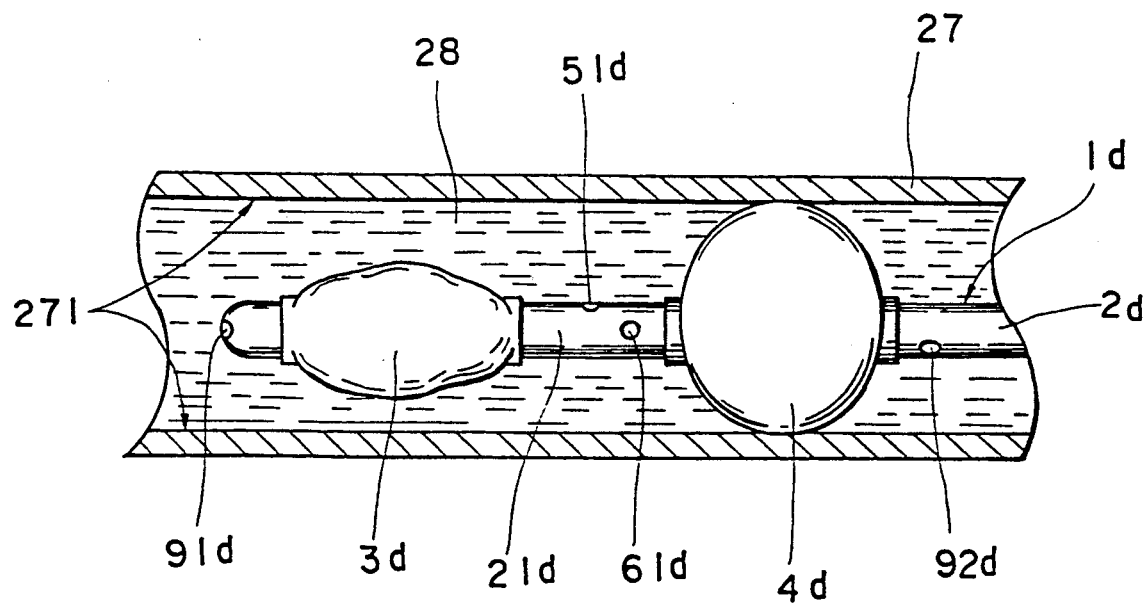
Figure 16:
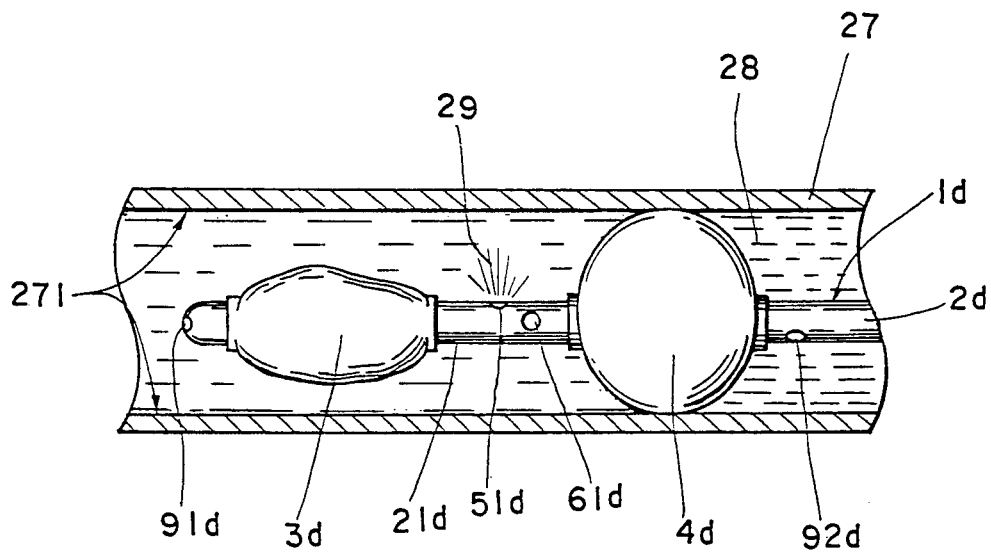
Figure 17:
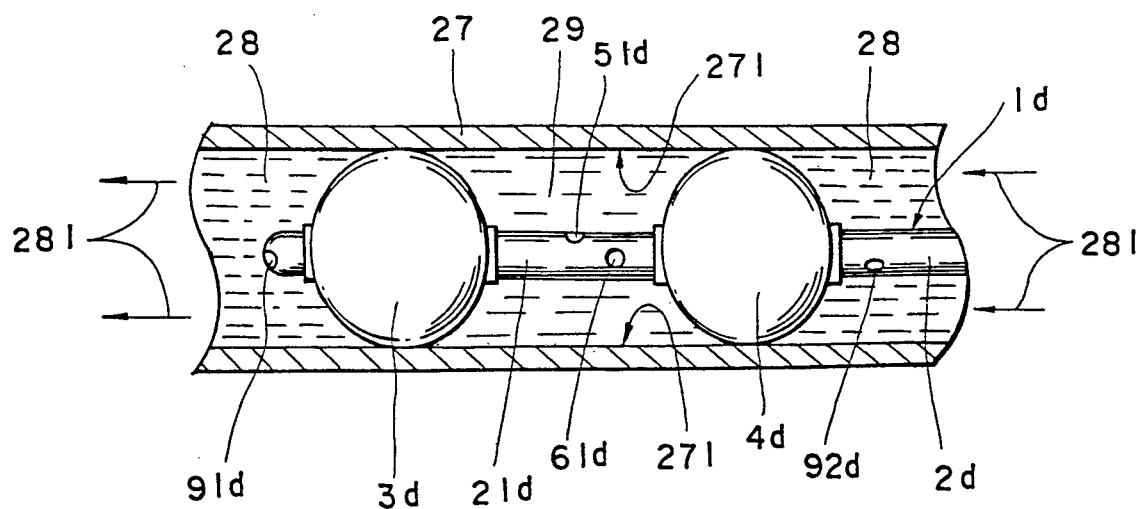

FIGS. 15, 16, and 17 are fragmental cross-sectional views showing the catheter tube of FIG. 12 during its use.

BEST MODE FOR CARRYING OUT THE INVENTION

The catheter tube of the present invention will be better understood from the following detailed description of its preferred embodiments taken in conjunction with the accompanying drawings.

It is to be noted that although the following description refers to the typical application of the catheter tube of the invention as an endoscope, the invention is not limited thereto.

FIRST EMBODIMENT

Figure 3:
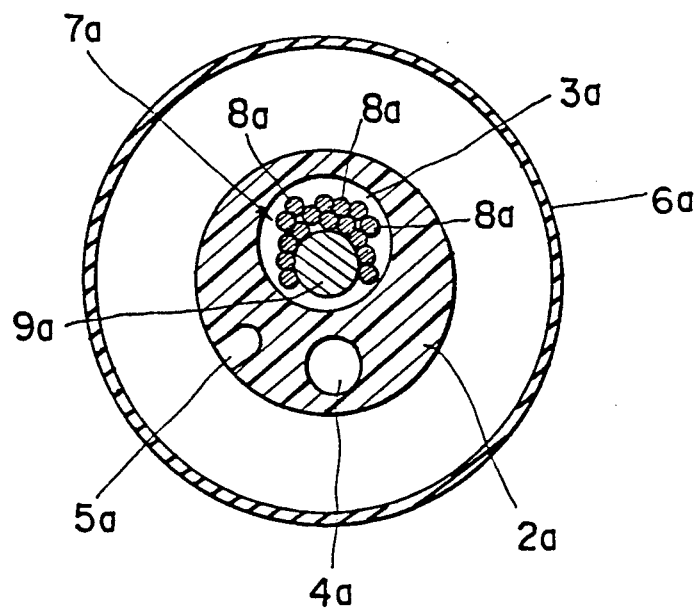
FIG. 3 is a cross-sectional view taken along lines III—III in FIG. 2.

FIG. 1 is a side view illustrating the construction of a catheter tube 1a according to the present invention, FIG. 2 is an axial cross-section showing the construction of a distal end portion of the catheter tube 1a, and FIG. 3 is a cross-section taken along lines III—III in FIG. 2.

As shown in these figures, the catheter tube 1a includes a tube body 2a and a balloon 6a attached to the tube body 2a around the outer peripheral wall thereof adjacent its distal end (at the left side in FIG. 1).

The balloon 6a is formed of a rubbery material such as silicone rubber and latex rubber, urethane, polyvinyl chloride, ethylene-vinyl acetate copolymer or the like so that it is inflatable and contractible.

The tube body 2a is formed of a flexible material, for example, polyvinyl chloride, polyurethane, silicone rubber, polyethylene, nylon, ethylene-vinyl acetate copolymer or the like.

The tube body 2a is formed with various lumens intended for different purposes and functions as will be described below.

An instrument accommodating lumen 3a is open at the distal end of the tube body 2a. A visualizing or therapeutic instrument for visualizing or medically treating the inner wall of a body cavity in the form of a bundle of optical fibers 7a is accommodated in the lumen 3a for movement in an axial direction of the tube body.

The optical fiber bundle 7a includes a light-transmitting fiber (or light guide) 8a and a light-receiving fiber (or image fiber) 9a and has a distal end 71a disposed near a distal opening 31a of the instrument accommodating lumen 3a as shown in FIG. 3. Light generated by a light source (not shown) at a proximal side (right side in FIG. 1) of the catheter tube 1a is conducted through the light-transmitting fiber 8a and projected from the distal end thereof toward a site to be visualized, and the reflected light is taken into the light-receiving fiber 9a at its distal end whereby the image is transmitted through the fiber 9a to an imaging section (not shown) at a proximal side of the catheter tube.

These light-transmitting and receiving fibers are optical fibers formed of quartz, plastics, multi-component glass or the like.

For smooth movement of the optical fiber bundle 7a through the instrument accommodating lumen 3a, the outer surface of the optical fiber bundle 7a and/or the inner surface of the instrument accommodating lumen 3a may preferably be subjected to a lubricating treatment.

The lubricating treatment includes coating of lubricants such as silicone oil, Teflon, olive oil, glycerin, and polyethylene glycol and a hydrophilic treatment.

A liquid injecting lumen 4a is open at the distal end of the tube body 2a and adapted to inject a fluid into the body cavity through an opening 41a or take in a fluid from the body cavity through the opening 41a. More particularly, the lumen 4a is used to administer a liquid medicament or similar fluid into the body cavity where the catheter tube 1a is inserted and indwelled, or utilized as a flash channel for injecting a clear liquid 29 of FIG. 8 (such as physiological saline) displacing the visibility impeding blood.

A balloon inflating lumen 5a communicates with the interior of a balloon 6a as shown in FIG. 3 and is adapted to deliver a fluid (which may be either a gas or a liquid, preferably a liquid for safety to be taken into account upon insertion into a blood vessel) into the balloon 6a for inflation and discharge the fluid from the balloon 6a for contraction.

The balloon 6a is dimensioned such that when inflated, it makes close contact with the inner wall 271 of FIG. 7 of the body cavity where the catheter tube is inserted, for securing the catheter tube 1a relative to the body cavity and for blocking a further flow of blood beyond the balloon 6a (toward the distal end of the tube) when the visibility impeding blood is purged or displaced by a clear liquid.

The balloon 6a is preferably designed so as to expand radially from the center of the tube body 2a when inflated.

The transverse cross section of balloon 6a may have a circular, elliptical or similar shape, but preferably a shape conforming to the transverse cross section of the body cavity where the catheter tube is inserted and indwelled because more tight contact with the body cavity is preferred.

To ensure tight fit of the balloon within the body cavity without a gap, the balloon 6a is dimensioned so as to meet the relationship: $Dmin \geq dmax$ wherein Dmin is the minimum diameter, that is, the diameter of a portion of the balloon which is minimum in a radial direction of the tube when the balloon 6a is inflated outside the body cavity and dmax is the maximum diameter, that is, the diameter of a portion of the inner wall of the body cavity which is maximum before the catheter tube is inserted therein (when the body cavity is contracted).

The tube body 2a may be provided with a plurality of longitudinally spaced balloons. The balloon 6a should manner. Possible attachment methods include adhesive manner and the possible attachment methods involve adhesive bonding of a separate member (an annular or bag-shaped rubber member or the like), tying with thread, integral molding or two-color molding together with the tube, and any other methods capable of liquid tight attachment of the balloon.

As shown in FIG. 1, the catheter tube 1a at the side of the proximal end 10a is branched into three tubes 11a, 12a, and 13a which communicate with the instrument accommodating lumen 3a, liquid injecting lumen 4a, and balloon inflating lumen 5a in the tube body 2a, respectively.

The tube 11a at its proximal end is connected to a connector tube 16a through a T-type joint 14a so that the optical fiber bundle 7a extends through the tube 11a, T-type joint 14a, and connector tube 16a. In turn, the connector tube 16a at its proximal end is provided with a manipulator 17a for axially moving the optical fiber bundle 7a through the tube body 2a and securing the optical fiber bundle 7a at the desired position relative to the tube body 2a. The manipulator 17a will be described in further detail.

Figure 4:
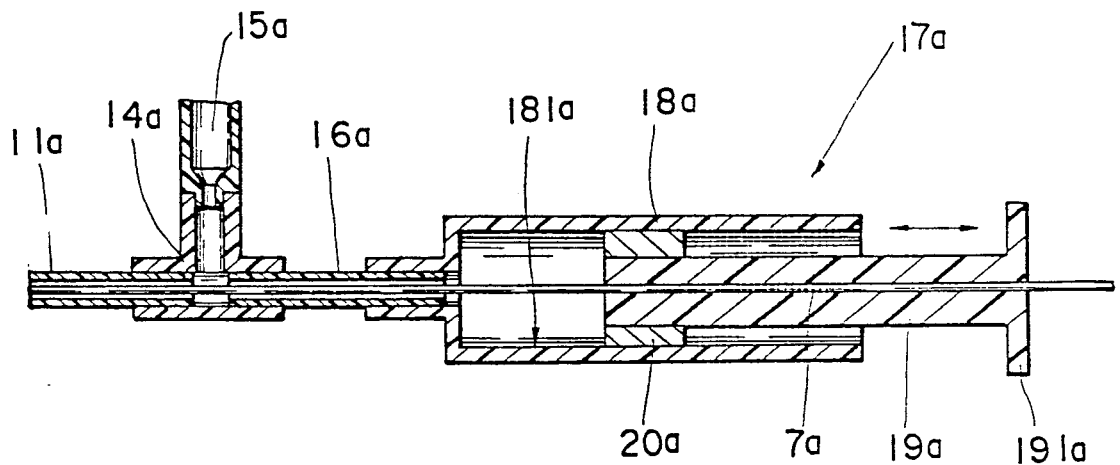
FIGS. 4 and 5 are axial cross-sectional views showing the construction of a proximal end portion of the catheter tube shown in FIG. 1.

FIG. 4 is an axial cross section showing the construction of one example of the manipulator 17a.

As shown in the figure, the manipulator 17a includes means for holding the proximal end side of the instrument accommodating lumen in a liquid tight manner (liquid tight holding member) and is comprised of a cylinder-shaped female connector segment 18a having one end connected to the proximal end of the connector tube 16a and a piston-shaped male connector segment 19a received in the bore of the female connector segment 18a through a sealing member 20a such as a rubber ring. The optical fitter bundle 7a is secured to the male connector segment 19a so that axial movement of the male connector segment 19a (in the direction of the double ended arrow in FIG. 4) causes the optical fiber bundle 7a to travel through the instrument accommodating lumen 3a in an axial direction of the tube body. The stroke of the optical fiber bundle 7a may be the range between the position where the distal end 71a of the optical fiber bundle 7a is retracted at a protective position within the instrument accommodating lumen 3a (the state being shown in FIG. 7) and the position where the distal end 71a of the optical fiber bundle 7a projects 0 to 20 mm beyond the distal opening 31a of the instrument accommodating lumen 3a (the state being shown in FIG. 8).

If the projection of the distal end 71a of the optical fiber bundle 7a beyond the distal opening exceeds 20 mm, the optical fiber bundle 7a could cause damage to the blood vessel wall or the fiber bundle itself could fail.

The stroke of the optical fiber bundle 7a may be set by regulating the connection where the optical fiber bundle 7a is secured to the male connector segment 19a.

The sealing member 20a is secured to the male connector segment 19a so that when the male connector segment 19a is axially moved, the sealing member 20a may slide along the inner surface 181a of the female connector segment 18a in tight contact relationship, thereby maintaining liquid tightness.

When the male connector segment 19a is at a stop, the optical fiber bundle 7a is held fixed relative to the tube body 2a.

The catheter tube 1a is utilized for observation by injecting a fluid, for example, a liquid such as physiological saline through a fluid injecting connector 15a mounted to the T-type joint 14a to fill the instrument accommodating lumen 3a, tube 11a, T-type joint 14a, connector tube 16a, and female connector segment 18a with the liquid.

The liquid is introduced for the purposes of preventing blood from entering the instrument accommodating lumen 3a through the distal opening 31a and preventing the blood which has entered the instrument accommodating lumen 3a from forming thrombi when the catheter tube 1a is inserted into a blood vessel and left therein. The sealing member 20a is thus provided in order to prevent the liquid or incoming blood from leaking out of the catheter tube 1a.

The sealing member 20 which is formed of an elastomeric material is in such close contact with the inner surface of the female connector segment 18a that the sealing member 20 is movable together with the male connector segment 19a when it is manipulated, but unmovable under the pressure of the liquid in the female connector segment 18a in a normal state.

Retainer means for retaining the male connector segment 19a may be provided.

Unlike the embodiment shown in FIG. 4, the manipulator 17a may be of the construction wherein a ring-shaped sealing member is joined to the inner surface 181a of a female connector segment 18a and a male connector segment 19a having a slightly larger outer diameter than the inner diameter of the ring is fitted within the ring.

Figure 5:
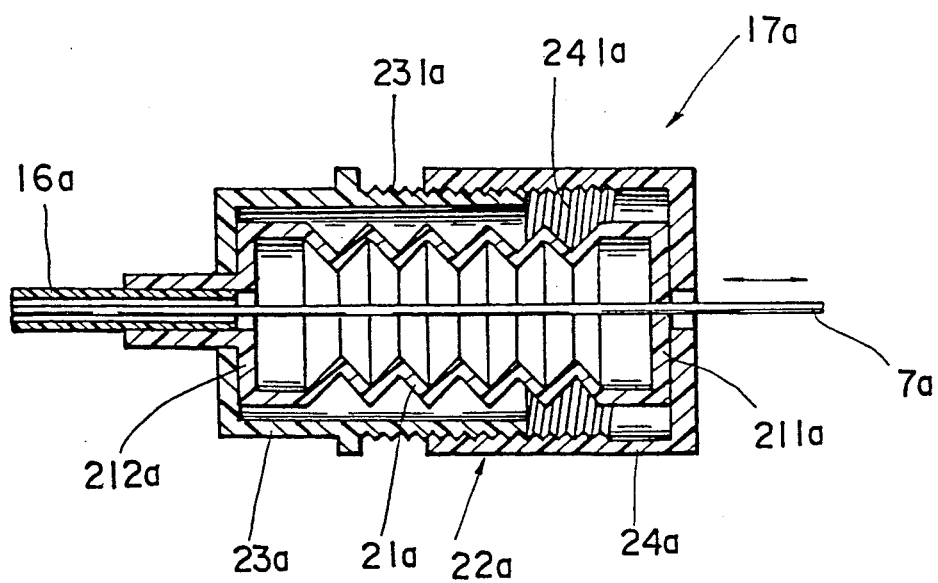

FIG. 5 is an axial cross section showing the construction of another example of the manipulator 17a. As shown in the figure, the connector tube 16a at its proximal end is connected to a expandable/contractible bellows 21a which is formed of ethylene-vinyl acetate copolymer, polyvinyl chloride, polyethylene or the like. The bellows 21a has a proximal end 211a to which the optical fiber bundle 7a is secured, whereby the optical fiber bundle 7a is movable in an axial direction of the tube body (in the direction of an arrow in FIG. 5) in response to expansion and contraction of the bellows 21a.

It is to be noted that the bellows 21a is of the closed type which ensures liquid tightness at the proximal end side of the instrument accommodating lumen 3a as in the previous example.

The bellows 21a is received within a holder 22a including a cylinder 23a and a lid 24a. The cylinder 23a and lid 24a are formed with female and male threads 231a and 241a, respectively, so that the lid 24a is threadably engaged with the cylinder 23a by turning the lid 24a, the extent of expansion of the bellows being limited by the number of turns of the lid. The reaction force of the bellows 21a causes the proximal and distal ends 211a and 212a of the bellows 21a to abut against the inside bottoms of the lid 24a and cylinder 23a, respectively. When the lid 24a is held against rotation, expansion of the bellows 21a is limited to a certain extent, that is, the position of the optical fiber bundle 7a relative to the tube body 2a is fixed.

It will be understood that the manipulator 17a previously described may be provided at any desired portion (for example, on the male connector segment 19a or holder 22a) with a scale for indicating the distance of travel of the optical fiber bundle 7a (or the distance of projection from the distal opening 31a).

Next, the operation of the catheter tube 1a is described.

FIGS. 6, 7, and 8 are fragmental cross-sectional views showing the catheter tube 1a of the invention during its use.

As shown in FIG. 6, the catheter tube 1a functioning as an endoscope is inserted into a body cavity, that is, a blood vessel 27 and left at a destined site therein. At this point, the distal end 71a of the optical fiber bundle 7a is retracted at a protective position within the instrument accommodating lumen 3a by manipulation through the manipulator 17a at the proximal side of the catheter tube 1a. The retracted positioning protects the distal end 71a, especially the light-receiving face of the optical fiber bundle from damage by contact with the guide catheter or the inner wall 271 of the blood vessel 27 when the catheter tube 1a is inserted or prevents the distal end 71a of the optical fiber bundle from injuring the inner wall 271 of the blood vessel 27.

Then, a fluid for inflating the balloon, for example, a liquid such as physiological saline or a gas such as $CO_2$ gas is supplied through a balloon connector 26a at the catheter tube proximal side and delivered into the balloon 6a through the tube 13a and the balloon inflating lumen 5a, thereby causing the balloon 6a to inflate as shown in FIG. 7.

The thus inflated balloon 6a makes close contact with the inner wall 271 of the blood vessel 27, thereby retaining the catheter tube 1a relative to the blood vessel 27 and shutting off a flow of blood 28 through the blood vessel 27.

Further, a clear liquid 29, for example, physiological saline is supplied through a flash connector 25a at the catheter tube proximal side, delivered through the tube 12a and liquid injecting lumen 4a, and injected through the opening 41a at the distal end of the tube body 2a, thereby displacing the blood 28 which has been present forward of the balloon 6a (on a distal side of the tube) and filling the volume with the clear liquid 29 instead.

Insofar as the minimum diameter of the balloon 6a when inflated is at least substantially equal to the maximum inner diameter of the blood vessel 27, the balloon 6a makes sufficiently tight contact with the inner wall 271 of the blood vessel 27 to prevent the blood 28 rearward of the balloon 6a (on a proximal side of the tube) from flowing forward of the balloon 6a, that is, to a site under observation, ensuring a clear image for observation.

Next, by grasping a manipulating flange 191a of the manipulator 17a on the catheter tube proximal side as shown in FIG. 4 and manipulating the male connector segment 19a, the optical fiber bundle 7a is moved through the instrument accommodating lumen 3a toward the distal end of the catheter tube 1a (in the direction of an arrow in FIG. 4) such that the distal end 71a of the optical fiber bundle projects a predetermined distance beyond the distal opening 31a of the instrument accommodating lumen 3a as shown in FIG. 8. Then the interior of the blood vessel 27 can be visualized through the light-transmitting and receiving fibers 8a and 9a with the view unimpeded by the inner wall of the instrument accommodating lumen 3a.

For observation, the distal end 71a of the optical fiber bundle may be located at the optimum visible position by adjusting the stroke of the male connector segment 19a. When it is desired to visualize another site of the blood vessel 27 spaced a predetermined distance from the initial site in a longitudinal direction of the blood vessel, the distal end 71a of the optical fiber bundle may be moved to the next site to be visualized by a similar operation. The operation is very simple since there is no need for causing the balloon 6a to contract to disengage the catheter tube 1a from the blood vessel 27 and moving the entire catheter tube 1a. It is to be noted that the instrument accommodating lumen 3a, tube 11a, T-type joint 14a, connector tube 16a, and female connector segment 18a are previously filled with a liquid (for example, physiological saline) supplied through the fluid injecting connector 15a, and the sealing member 20a interposed between the female and male connector segments 18a and 19a prevents leakage of the liquid or the blood entering through the distal opening 31a and mixing with the liquid.

In a normal condition (without an external force applied to the male connector segment), the male connector segment 19a is fastened to the female connector segment 18a by the resiliency of the sealing member 20a, whereby the optical fiber bundle 7a is held fixed relative to the tube body 2a.

When the manipulator 17a shown in FIG. 5 is utilized, the optical fiber bundle 7a is moved a predetermined distance toward the distal end of the catheter tube 1a by rotating predetermined turns the lid 24a of the holder 22a with respect to the cylinder 23a to contract the bellows 21a.

Also in this case, no leakage of the filling liquid occurs because of the closed type of the bellows 21a.

SECOND EMBODIMENT

FIG. 9 is an axial cross-sectional view of a catheter tube 1c according to the present invention, and FIG. 10 is a cross-sectional view taken along lines X—X in FIG. 9.

In the description of this embodiment, the description of the same elements as in the first embodiment is omitted.

As shown in FIGS. 9 and 10, the catheter tube 1c includes a tube body 2c and a balloon 3c attached to the tube body 2c around the outer peripheral wall thereof adjacent its distal end (at the left side in FIG. 9).

The nature and material of the balloon 3c and tube body 2c are the same as in the previous embodiment.

The tube body 2c is formed with a multi-purpose lumen 4c which is open at the distal end of the tube body. The multi-purpose lumen 4c performs multiple functions to be described below. The multi-purpose lumen 4c has accommodated therein a bundle of optical fibers 7c serving as a visualizing or therapeutic instrument for visualizing or medically treating the inner wall of a body cavity. The optical fiber bundle 7c has the same construction as in the previous embodiment and its distal end is disposed near a distal opening 6c of the tube body 2c.

Within the multi-purpose lumen 4c is defined a gap 41c between the optical fiber bundle 7c accommodated therein and the inner wall of the multi-purpose lumen 4c. The gap 41c plays the role of a channel for delivering a fluid, especially a clear liquid (e.g., physiological saline) for displacing blood from a space in the blood vessel under observation. More particularly, a clear liquid 29 is supplied into the multi-purpose lumen 4c from the catheter tube proximal side, passed through the gap 41c of the multi-purpose lumen 4c, and injected through the distal opening 6c.

It is to be noted that the multi-purpose lumen 4c is not only used as a flash channel for injecting the clear liquid, but also used for other purposes of administering a medicament liquid into the body cavity where the catheter tube is inserted and indwelled, taking in any fluid from the body cavity or the like.

In order that the multi-purpose lumen 4c allow for smooth passage of clear liquid or the like, the inner diameter of the multi-purpose lumen 4c should preferably be in a preferred range in relation to the outer diameter of the optical fiber bundle 7c. More specifically, the inner diameter of the multi-purpose lumen 4c is preferably 1.1 to 5.0 times the outer diameter of the optical fiber bundle 7c. The reason is that with an inner diameter of less than 1.1 times, the transverse cross sectional area of the gap 41c is too small to provide smooth channeling of clear liquid and that with an inner diameter of more than 5.0 times, the outer diameter of the tube body 2c is accordingly increased against the demand for a thin catheter tube.

The tube body 2c is formed with a side aperture 5c communicating the interior of the multi-purpose lumen 4c with the interior of the balloon 3c. Then a part of the clear liquid flowing through the multi-purpose lumen 4c enters the balloon 3c through the side aperture 5c, causing the balloon 3c to inflate under the liquid pressure. In this way, the multi-purpose lumen 4c has an additional function as a channel for a balloon inflating liquid (in this embodiment, the clear liquid for displacing the blood also serves as the balloon inflating liquid). If the tube body 2c is provided with a plurality of longitudinally spaced-apart balloons, side apertures 5c are formed for all the balloons or selected balloons, with at least one side aperture for each balloon.

The shape, number, and open area of the side aperture 5c are not particularly limited although the total open area should preferably allow delivery of a sufficient volume of fluid (clear liquid) to inflate the balloon 3c.

As understood from the foregoing description, the catheter tube of this embodiment utilizes the single multi-purpose lumen 4c which adopts multiple functions, that is, three functions of a space for accommodating a visualizing or therapeutic instrument (optical fiber bundle 7c), a channel for clear liquid for blood displacement, and a channel for balloon inflating liquid. As compared with the prior art catheter tube in which these three functions are performed by discrete special lumens, the present catheter tube can be reduced in diameter because the number of necessary lumens is reduced.

With respect to its function, shape, size, number, and attachment, the balloon 3c on the tube body 2c is the same as in the previous embodiment.

Next, the operation of the catheter tube 1c is described.

FIG. 11 is a fragmental cross-sectional view showing the catheter tube 1c during its use.

As shown in the figure, the catheter tube 1c functioning as an endoscope is inserted into a body cavity, that is, a blood vessel 27 and a clear liquid 29 such as physiological saline is supplied into the multi-purpose lumen 4c from the proximal side. The clear liquid 29 then flows through the gap 41c in the multi-purpose lumen 4c in the direction of an arrow in the figure, ejects into the blood vessel 27 through the distal opening 6c and at the same time, enters the balloon 3c through the side aperture 5c to inflate the balloon 3c.

The thus inflated balloon 3c makes close contact with the inner wall of the blood vessel 27, thereby retaining the catheter tube 1c relative to the blood vessel 27 and shutting off a flow of blood 28 through the blood vessel 27.

The space in the blood vessel forward of the balloon 3c (on the distal side of the tube) is filled with the clear liquid 29 which has displaced the visibility impeding blood.

Under such conditions, the interior of the blood vessel 27 can be visualized through light-transmitting and receiving fibers 8c and 9c.

The size of the inflated balloon 3c is determined in relation to the blood shutting off ability as in the previous embodiment.

THIRD EMBODIMENT

FIG. 12 is a side view showing the configuration of a catheter tube 1d according to the present invention, and FIG. 13 is an axial cross-sectional view of the catheter tube (in which lumens are shown in juxtaposition for ease of understanding).

In the description of this embodiment, the description of the same elements as in the first embodiment is omitted.

As shown in FIG. 12, the catheter tube 1d includes a tube body 2d, a first balloon 3d attached to the tube body 2d around the outer peripheral wall thereof adjacent its distal end (on the left side in FIG. 12), and a second balloon 4d attached to the tube body 2d around the outer peripheral wall thereof at a predetermined spacing from the first balloon 3d toward the proximal side (on the right side in FIG. 12).

The nature and material of the first and second balloons 3d and 4d and tube body 2d are the same as previously described.

The tube body 2d is formed with a plurality of lumens serving for different purposes and functions to be described below.

A liquid injecting lumen 5d which serves for the same function as previously described terminates at an opening 51d in any desired portion of the tube outer peripheral wall 21d between the first and second balloons 3d and 4d.

An instrument accommodating lumen 6d is to accommodate a bundle of optical fibers 12d serving as a visualizing or therapeutic instrument for visualizing or medically treating the inner wall of a body cavity. Since the inner wall of the body cavity is visualized between the first and second balloons 3d and 4d, the instrument accommodating lumen 6d terminates at an opening 61d in any desired portion of the tube outer peripheral wall 21d between the first and second balloons 3d and 4d.

The optical fiber bundle 12d has the same construction as previously described and its distal end is disposed near the opening 61d. (The optical fiber bundle is omitted in FIG. 13.)

A balloon inflating lumen 7d communicates with the interior of the first balloon 3d as shown in FIG. 13 and functions as a channel for a fluid for inflating and contracting the first balloon 3d. Similarly, a balloon inflating lumen 8d communicates with the interior of the second balloon 4d and functions for inflating and contracting the second balloon 4d.

Instead of discrete balloon inflating lumens 7d and 8d for respective balloons 3d and 4d, it is possible to form a single balloon inflating lumen in communication with both the balloons 3d and 4d whereby the balloons 3d and 4d are inflated or contracted with a time lag. In one exemplary configuration, the communicating openings of the balloon inflating lumen to the balloons 3d and 4d have different degrees of openness so that introduction of balloon inflating liquid under a certain pressure causes the balloon 4d to inflate first and the balloon 3d to subsequently inflate.

The mechanism for the inflation and contraction of the first and second balloons is not necessarily limited to a lumen or lumens extending through the tube body 2d, and instead, a tube or tubes having a gas or liquid channeling lumen in communication with the balloons 3d and 4d may be provided outside the tube body 2d.

A first opening 91d is defined at any desired portion of the tube body 2d located distal or forward of the first balloon 3d (which may be either the distal end or the outer peripheral wall 21d of the tube). A second opening 92d is defined in the outer peripheral wall 21d of the tube body 2d located proximal or rearward of the second balloon 4d. A bypass lumen 9d providing communication between the first and second openings 91d and 92d is defined in the tube body 2d.

The bypass lumen 9d allows for flow communication between the blood 28 in the blood vessel on the side distal of the first balloon 3d and the blood 28 on the side proximal of the second balloon 4d (see FIG. 17).

The outer diameter of the tube body 2d and the inner diameters of the respective lumens 5d, 6d, 7d, 8d, and 9d may be suitably determined in consideration of the inner diameter of the body cavity (blood vessel 27) where the catheter tube is to be inserted. Among others, the bypass lumen 9d should preferably have an inner diameter of at least 0.3 mm because an inner diameter of smaller than 0.3 mm obstructs a smooth blood flow.

The first and second balloons 3d and 4d make close contact with the inner wall of the body cavity, when inflated, thereby accomplishing the functions of retaining the catheter tube 1d relative to the body cavity and shutting off a further flow of blood, thereby allowing a clear liquid to displace the visibility impeding blood from between the first and second balloons 3d and 4d.

The shape, size, and attachment of the first and second balloons 3d and 4d are the same as previously described.

The spacing S between the first and second balloons 3d and 4d is preferably 1 to 100 mm. The reason is that with a spacing S of more than 100 mm, the lumen 9d has a longer bypass distance, imparting an increased flow resistance and requiring an increased amount of clear liquid flashed leading to a loss of safety to the human body. With a spacing S of less than 1 mm, the blood vessel wall can be visualized with difficulty.

Next, the operation of the catheter tube 1d is described.

FIGS. 15, 16, and 17 are fragmental cross-sectional views showing the catheter tube 1d during its use.

As shown in FIG. 15, the catheter tube 1d functioning as an endoscope is inserted into a body cavity, that is, a blood vessel 27 and a fluid is supplied into the second balloon 4d through the balloon inflating lumen 8d to inflate the second balloon 4d. Then the second balloon 4d makes close contact with the inner wall 271 of the blood vessel 27, thereby retaining the catheter tube 1d relative to the blood vessel 27 and shutting off a further flow of blood 28 through the blood vessel 27 (to either the left or the right in the figure).

At this point, a clear liquid 29 such as physiological saline is injected from the liquid injecting lumen 5d through the opening 51d as shown in FIG. 16, thereby displacing the blood on the distal side of the second balloon 4d and filling the space with the clear liquid 29 instead.

Next, a fluid is supplied into the first balloon 3d through the balloon inflating lumen 7d to inflate the first balloon 3d as shown in FIG. 17, causing the first balloon 3d to make close contact with the inner wall 271 of the blood vessel 27.

At this point, the space in the blood vessel 27 between the first and second balloons 3d and 4d is filled with the clear liquid 29 instead of the visibility impeding blood. Thus the inner wall 271 of the blood vessel can be visualized through light-transmitting and receiving fibers 10d and 11d projecting from the opening 61d in the outer peripheral wall 21d of the tube body.

The size of the inflated first and second balloons 3d and 4d is determined in relation to the blood shutting off ability as previously described.

The inner wall 271 of the blood vessel 27 can be visualized over the entire circumference by rotating the catheter tube 1d itself within the blood vessel 27.

In turn, the blood 28 on the distal side of the first balloon 3d and the blood 28 on the proximal side of the second balloon 4d can communicate with each other through the bypass lumen 9d. If the blood is flowing in the direction of arrows 281 in FIG. 17, the blood 28 on the proximal side of the second balloon 4d passes through the bypass lumen 9d from the second opening 92d to the first opening 91d and comes out to the distal side of the first balloon 3d. This ensures a continuous flow of blood through the blood vessel 27 during observation, enabling observation over an extended period of time.

Since the portion of the blood vessel to be visualized is delimited between the first and second balloons 3d and 4d in close contact with the blood vessel inner wall 271, no blood 28 can mix with the clear liquid 29 between the balloons, ensuring clear visibility.

Although visualization of the interior of the blood vessel through light-transmitting and receiving fibers has been described in connection with the first to third embodiments, the catheter tube of the present invention is not limited to this application, but may be utilized in a wide variety of applications including administration of liquid medicament, irradiation of laser beams through optical fibers, tip guidance upon insertion to a destined site, and the like.

Examples of the present invention are given below by way of illustration.

EXAMPLE 1

A catheter tube of the structure shown in FIGS. 1, 2, 3, and 4 was manufactured. Various parameters of this catheter tube are described below.

<Tube body>

Material: polyvinyl chloride containing a radiopaque agent
Outer diameter: about 2.5 mm
Entire length: about 1.5 m
Lumen 3 lumens
    Clear liquid injecting lumen: 1
    Fiber accommodating lumen (inner diameter 1.2 mm): 1
    Balloon inflating lumen: 1
Instrument in lumen:
    A single optical fiber bundle having an outer diameter of about 0.8 mm was prepared by integrally joining an image fiber (a bundle of about 2,000 quartz fibers of about 2.3 $\mu$m in diameter) and a light guide (a bundle of 25 quartz fibers of about 50 $\mu$m in diameter). A convex lens was mounted on the end face of the image fiber such that the lens received the light emitted from the light guide and formed the image of an object on the end face of the image fiber.

<Balloon>

Material: latex rubber

Thickness: about 150 μm
Shape: cylindrical
Effective length: 7 mm
Inflated diameter: 6 mm
    Attachment: tied to the tube body with thread <Catheter tube proximal side>

Manipulator: structure shown in FIG. 3
Cylinder-shaped female connector segment:
    Entire length: 40 mm
    Inner diameter: 7.8 mm
Piston-shaped male connector segment:
    Entire length: 40 mm
    Outer diameter: 7.2 mm
Sealing member:
    Silicone rubber ring (bonded to the male connector segment)
    Outer diameter: 8.0 mm
    Inner diameter: 7.0 mm
Stroke: 30 mm An eyepiece was mounted to the proximal end of the image fiber through an image connector 91a, enabling direct observation. The proximal end of the light guide was coupled to a light connector 81a which was connected to a white light source. The proximal end of the tube connected to the clear liquid injecting lumen was coupled to a cock having a Luer tapered socket (flash connector 25a), to which a syringe A1 was connected such that physiological saline could be supplied to the lumen. The proximal end of the tube connected to the lumen leading to the balloon was coupled to a valve having a Luer tapered socket (balloon connector 26a), to which a syringe B was connected such that inflating fluid (physiological saline) could be injected into the balloon.

The catheter tube of such construction was inserted into a blood vessel having an inner diameter of about 5 mm with the distal end of the optical fiber bundle retracted within the lumen. First the syringe B1 was manually operated, causing the balloon to inflate, thereby retaining the catheter tube relative to the blood vessel and shutting off a blood flow. Then the syringe A1 was operated to inject 1.5 ml of physiological saline into the blood vessel, causing the balloon to inflate, thereby retaining the catheter tube relative to the blood vessel and shutting off a blood flow.

The volume of the blood vessel defined forward of the balloon was filled with the saline.

Next, the male connector segment of the manipulator was operated to move the optical fiber bundle 1.5 cm toward the distal end of the catheter tube whereby the distal end of the optical fiber bundle projected about 1 cm beyond the distal opening of the lumen.

The inner wall of the blood vessel could be observed by looking into the eyepiece or watching the video monitor screen, resulting in clear visualization without entry of blood into the zone under observation.

EXAMPLE 2

A catheter tube of the structure shown in FIGS. 9 and 10 was manufactured. Various parameters of this catheter tube are described below.

<Tube body>

Material: polyvinyl chloride containing a radiopaque agent
Outer diameter: about 1.4 mm
Entire length: about 1.5 m
Lumen: one multi-purpose lumen
Lumen inner diameter: 1.0 mm
Instrument in lumen: same as in Example 1

<Balloon>

Material: silicone rubber
Thickness: about 150 μm
Shape: cylindrical
Effective length: 7 mm
Inflated diameter: 6 mm <Side aperture>

Number: 1
Open area: about 1 mm$^2$

<Catheter tube proximal side>

An eyepiece was mounted to the proximal end of the image fiber, enabling direct observation. The proximal end of the light guide was coupled to a light connector which was connected to a white light source. The proximal end of the multi-purpose lumen was coupled to a cock having a Luer tapered socket, to which a syringe A3 was connected such that physiological saline could be supplied to the multi-purpose lumen.

The catheter tube of such construction was inserted into a blood vessel having an inner diameter of about 3 mm.

Then the syringe A3 was operated to inject 1.5 ml of physiological saline into the blood vessel, causing the balloon to inflate, thereby retaining the catheter tube relative to the blood vessel and shutting off a blood flow.

The volume of the blood vessel defined forward of the balloon (on the distal side of the tube) was filled with the saline. In this condition, the inner wall of the blood vessel could be observed by looking into the eyepiece or watching the video monitor screen, resulting in clear visualization without entry of blood into the zone under observation.

EXAMPLE 3

A catheter tube of the structure shown in FIGS. 12, 13, and 14 was manufactured. Various parameters of this catheter tube are described below.

<Tube body>

Material: polyvinyl chloride containing a radiopaque agent
Outer diameter: about 2.5 mm
Entire length: about 1.5 m
Lumen: 5 lumens
    Clear liquid injecting lumen: 1
    Fiber accommodating lumen: 1
    First balloon inflating lumen: 1
    Second balloon inflating lumen: 1
    Bypass lumen (inner diameter 1.2 mm): 1
Instrument in lumen: The same optical fiber bundle as in Example 1 was used except that the outer diameter of the bundle was changed to about 0.9 mm.

<First balloon>

Material: latex rubber
Thickness: about 150 μm
Shape: cylindrical
Effective length: 7 mm
Inflated diameter: 6 mm <Second balloon>

Material: latex rubber
Thickness: about 150 μm
Shape: cylindrical
Effective length: 7 mm
Inflated diameter: 6 mm
Spacing S from the first balloon: 25 mm <Catheter tube proximal side>

An eyepiece was mounted to the proximal end of the image fiber, enabling direct observation. The proximal end of the light guide was coupled to a light connector which was connected to a white light source. The proximal end of the clear liquid injecting lumen was coupled to a cock having a Luer tapered socket, to which a syringe A4 was connected such that physiological saline could be supplied to the lumen. The proximal ends of the lumens leading to the first and second balloons were coupled to valves each having a Luer tapered socket, respectively, to which syringes B4 and C4 were connected such that inflating fluid (physiological saline) could be injected into the respective balloons. The catheter tube of such construction was inserted into a blood vessel having an inner diameter of about 5 mm. First the syringe C4 was manually operated to inflate the second balloon, thereby retaining the catheter tube relative to the blood vessel and shutting off a blood flow.

Then the syringe A4 was operated to inject 1.5 ml of physiological saline into the blood vessel on the distal side of the first balloon to displace the blood.

Thereafter, the syringe B4 was manually operated to inflate the first balloon. The space defined between the first and second balloons was filled with the saline.

In this condition, the inner wall of the blood vessel could be observed by looking into the eyepiece or watching the video monitor screen, resulting in clear visualization without entry of blood into the zone under observation.

The time required for observation was about 1 minute. A continuous blood flow occurred in the blood vessel through the bypass lumen during observation.

INDUSTRIAL APPLICABILITY

The first form of the invention provides a catheter tube wherein a visualizing or therapeutic instrument in the form of a bundle of optical fibers is movable through a tube body in an axial direction thereof and a manipulator is provided for retaining the optical fiber bundle at a predetermined position relative to the tube body such that the distal end of the optical fiber bundle is retractable in a lumen when the catheter tube is inserted into a body cavity, and the distal end of the optical fiber bundle is projectable a predetermined distance from the lumen when the interior of the body cavity is visualized, thereby preventing any damage to the distal face of the optical fiber bundle upon insertion into the body cavity and ensuring clear visualization over a wide field.

The visualizing or therapeutic instrument is positioned by means of the manipulator on the proximal side of the catheter tube, avoiding the drawback of the prior art catheter tube that the distal end or light-receiving face of optical fibers is contaminated with an adhesive for bonding the optical fibers, resulting in a visual image with a reduced clearness.

Further when it is desired to change the site to be observed (in a longitudinal direction of the body cavity), only the visualizing instrument may be moved by means of the manipulator. The site to be observed can be altered by a very simple operation since there is no need for cumbersome operation of moving the catheter tube itself.

The second form of the invention provides a catheter tube wherein a multi-purpose lumen commonly serves to accommodate a visualizing or therapeutic instrument such as an optical fiber bundle, to channel a fluid such as a clear liquid, and to channel a balloon inflating fluid, reducing the number of necessary lumens, thus allowing the catheter tube to be reduced in diameter. When the catheter tube is used as an endoscope, body cavities with a smaller inner diameter, for example, blood vessels, ureter, and bile duct can be visualized. Observation is practised through a simple process since a single operation can accomplish both inflation of the balloon for shutting off a blood flow and injection of a clear liquid for displacing blood from the zone to be visualized.

The third form of the invention provides a catheter tube wherein the interior of the body cavity is visualized or medically treated within the boundary delimited by first and second balloons. When the inner wall of the blood vessel is visualized by an endoscope, for example, a clear observation is possible without the risk that the visibility impeding blood would mix with the clear liquid charged between the first and second balloons.

Where the tube body is formed with a bypass lumen, this bypass lumen provides flow communication between the fluid (e.g., blood in the case of a blood vessel) on the distal side of the first balloon and the fluid on the proximal side of the second balloon even during observation of the body cavity interior.

This feature of the invention of maintaining a continuous flow of blood during observation provides an endoscope capable of long-term observation although long-term observation is not recommended for safety of the human body with the prior art endoscope which requires to shut off a blood flow through the blood vessel during observation.

Therefore, the catheter tube of the invention enables clear visualization over a wide field, diameter reduction, long-term observation and it is useful as a catheter tube for visualizing or medically treating body cavities with a smaller inner diameter, for example, blood vessels, ureter, and bile duct.

We claim:

1. A catheter tube for insertion into a body cavity, comprising:

a tube body having an axis, an outer peripheral wall, an open distal end portion, and a proximal end portion;

at least one inflatable and contractible balloon attached around the outer peripheral wall adjacent the open distal end portion of said tube body;

at least one lumen defined in said tube body and open to the open distal end portion of said tube body for accommodating at least one instrument therein;

a further lumen defined in said tube body in fluid communication with the interior of said balloon for inflating said balloon:

the at least one instrument accommodated in said at least one accommodating lumen enabling at least one of visualizing and medically treating the interior of the body cavity; and fluid-tight manipulator means provided at the proximal end portion of said catheter tube for moving the instrument through the tube body along the axis of the tube body and for positioning said instrument at a selected position relative to said tube body while maintaining said at least one accommodating lumen fluid-tight at the proximal end portion thereof, said fluid-tight manipulator means including:
- a closed bellows connected to be in communication with said at least one accommodating lumen at the proximal end portion of said tube body, said closed bellows having the at least one instrument secured therein at the proximal end portion of said tube body; and
- a holder receiving said bellows for limiting the extent of expansion of said bellows, said holder including a cylinder member and a lid member provided with an external and an internal thread, respectively, the lid member being threadably engaged on the cylinder member so that the fluid-tight manipulator means is compressed and expanded by turning the lid member.

2. A catheter tube as set forth in claim 1, wherein:
said at least one instrument includes a bundle of optical fibers; and
the at least one lumen having an inner diameter which is 1.1 to 3.0 times larger than the outer diameter of the optical fiber bundle.

3. A catheter tube as set forth in claim 2, wherein the bundle of optical fibers has an outer surface, and further comprising a lubricant on said outer surface of said bundle of optical fibers.

4. A catheter tube as set forth in claim 3, wherein the at least one accommodating lumen has an inner surface, and wherein the lubricant is on both the outer surface of said optical bundle and on the inner surface of said at least one lumen.

5. A catheter tube as set forth in claim 2, wherein the at least one accommodating lumen has an inner surface, further comprising a lubricant on said inner surfaces of said at least one lumen.

6. A catheter tube as set forth in claim 1, wherein the at least one instrument comprises a visualization instrument for viewing an area in the body cavity.

7. A catheter tube as set forth in claim 1, wherein said at least one instrument comprises a therapeutic instrument for treating the body cavity after the at least one instrument is inserted in the body cavity.

8. A catheter tube as set forth in claim 1, wherein the fluid-tight manipulator means moves the at least one instrument from a protective position at which the distal end of said at least one instrument is within said at least one accommodating lumen to a position at which the distal end of said at least one instrument projects from greater than 0 to not more than 20 mm beyond the open distal end portion of said at least one accommodating lumen.

9. A catheter tube as set forth in claim 1, wherein:
another inflatable and contractible balloon is positioned at the proximal end portion of said tube body; and
said another balloon is spaced 1 to 100 mm from said at least one inflatable and contractible balloon positioned at the open distal end portion of said tube body.

10. A catheter tube as set forth in claim 1, wherein the at least one inflatable and contractible balloon when inflated, has a minimum diameter which is at least substantially equal to a maximum inner diameter of the body cavity into which the catheter tube is to be inserted.

11. A catheter for insertion into a body cavity, comprising:
- a tube body having an axis, an outer peripheral wall, an open distal end portion, and a proximal end portion;
- a lumen defined in said tube body and open to the open distal end portion of said tube body;
- an instrument accommodated in said lumen, said instrument enabling at least one of visualizing and medically treating an interior of the body cavity; and
- fluid-tight manipulator means provided at the proximal end portion of said catheter tube for moving the instrument through said tube body along the axis of said tube body and for positioning said instrument at a selected position relative to said tube body while maintaining said lumen fluid-tight at the proximal end portion thereof, said fluid-tight manipulator means including:
  - a closed and expandable bellows connected to be in communication with said lumen at the proximal end portion of said tube body, said closed bellows having said instrument secured therein at the proximal end portion of said tube body; and
- a holder receiving said bellows for limiting the extent of expansion of said bellows, said holder including a cylinder member and a lid member provided with an external and an internal thread, respectively, the lid member being threadably engaged on the cylinder member so that the fluid-tight manipulator means is compressed and expanded by turning the lid member relative to the cylinder member.

12. A catheter as set forth in claim 11, wherein:
said instrument includes a bundle of optical fibers; and
the lumen has an inner diameter which is 1.1 to 3.0 times larger than the outer diameter of the optical fiber bundle.

13. A catheter as set forth in claim 12, wherein the bundle of optical fibers has an outer surface, and further comprising a lubricant on said outer surface of said bundle of optical fibers.

14. A catheter tube as set forth in claim 13, wherein the lumen has an inner surface, and wherein the lubricant is on both the outer surface of said optical bundle and on the inner surface on the lumen.

15. A catheter as set forth in claim 12, wherein the lumen has an inner surface, and further comprising a lubricant on said inner surfaces of the lumen.

16. A catheter as set forth in claim 11, wherein the instrument comprises a visualization instrument for viewing an area in the body cavity.

17. A catheter as set forth in claim 11, wherein the instrument comprises a therapeutic instrument for treating the interior of the body cavity after the instrument is inserted in the body cavity.

18. A catheter as set forth in claim 11, wherein the fluid-tight manipulator means moves the instrument from a protective position at which a distal end of the instrument is within the lumen to a position at which the distal end of the instrument projects from greater than 0 to not more than 20 mm beyond the open distal end portion of the lumen.

* * * * *